(12) United States Patent
Karamchedu et al.

(10) Patent No.: US 8,510,387 B2
(45) Date of Patent: Aug. 13, 2013

(54) HETEROGENEOUS RELATED DOCUMENT ATTACHING FOR (CLINICAL) MESSAGING

(75) Inventors: Murali M. Karamchedu, Beaverton, OR (US); Jeffrey B. Sponaugle, Hillsboro, OR (US); James Vincent Coppa, Portland, OR (US)

(73) Assignee: Kryptiq Corporation, Hillsboro, OR (US)

( * ) Notice: Subject to any disclaimer, the term of this patent is extended or adjusted under 35 U.S.C. 154(b) by 1773 days.

(21) Appl. No.: 11/194,117

(22) Filed: Jul. 29, 2005

(65) Prior Publication Data

US 2007/0038706 A1    Feb. 15, 2007

(51) Int. Cl.
*G06F 15/16*      (2006.01)
(52) U.S. Cl.
USPC .............................. 709/206; 707/4; 707/104.1

(58) Field of Classification Search
USPC .................................. 709/206; 707/4, 104.1
See application file for complete search history.

(56) References Cited

U.S. PATENT DOCUMENTS

| | | | |
|---|---|---|---|
| 2002/0103811 A1* | 8/2002 | Fankhauser et al. | 707/104.1 |
| 2004/0153515 A1* | 8/2004 | Touboul et al. | 709/206 |
| 2005/0187973 A1* | 8/2005 | Brychell et al. | 707/104.1 |

* cited by examiner

*Primary Examiner* — Kyung H Shin
(74) *Attorney, Agent, or Firm* — Schwabe, Williamson & Wyatt, P.C.

(57) ABSTRACT

Embodiments of the present invention provide methods and apparatuses for messaging with heterogeneous inter-related attachments. Embodiments provide messaging systems, devices and methods for electronic messaging with attachments containing, for example, documents created from a translating print driver and/or documents containing identifiers associating the documents to a subject.

17 Claims, 3 Drawing Sheets

HETEROGENEOUS RELATED DOCUMENT ATTACHING FOR (CLINICAL) MESSAGING

TECHNICAL FIELD

Embodiments of the present invention relate to the field of data processing, and, in particular, to methods and apparatuses for messaging with heterogeneous related attachments.

BACKGROUND

With advances in integrated circuit, microprocessor, networking and communication technologies, an increasing number of devices, in particular, digital computing devices, are being interconnected. This increased interconnectivity of computing devices has laid the groundwork for a communication infrastructure particularly well suited for electronic communications between such computing devices. More specifically, the increased interconnectivity of computing devices has led to the near ubiquitous adoption of electronic mail (email) as a standard mode of communication.

In the past, electronic mail communications were limited to the exchange of text-based messages between a relatively small populous. Over time, however, email applications and associated communications protocols have become increasingly sophisticated enabling more complex messages to be exchanged between larger numbers of individuals. For example, in addition to enabling the exchange of simple text-messages, many modern day email clients allow users to exchange complex, multipart MIME (Multipurpose Internet Mail Extensions) encoded files as well as a wide variety of binary attachments. Furthermore, with the introduction of web-based email clients that utilize World Wide Web protocols, such as the hypertext transmission protocol (HTTP) for the exchange of messages, access to email has become even more prolific.

BRIEF DESCRIPTION OF THE DRAWINGS

Embodiments of the present invention will be readily understood by the following detailed description in conjunction with the accompanying drawings. To facilitate this description, like reference numerals designate like structural elements. Embodiments of the invention are illustrated by way of example and not by way of limitation in the figures of the accompanying drawings.

DETAILED DESCRIPTION OF EMBODIMENTS OF THE INVENTION

Figure 1:
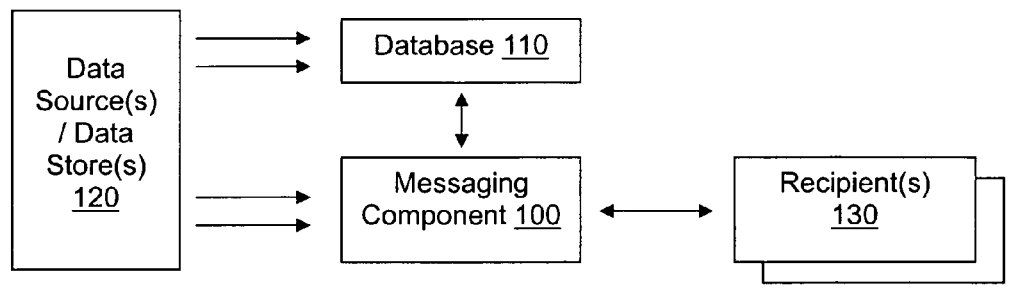
FIG. 1 illustrates a messaging system in accordance with an embodiment of the present invention.

In the following detailed description, reference is made to the accompanying drawings which form a part hereof wherein like numerals designate like parts throughout, and in which is shown by way of illustration embodiments in which the invention may be practiced. It is to be understood that other embodiments may be utilized and structural or logical changes may be made without departing from the scope of the present invention. Therefore, the following detailed description is not to be taken in a limiting sense, and the scope of embodiments in accordance with the present invention is defined by the appended claims and their equivalents.

The description is presented, in part, in terms of operations performed by a processor based device, using terms such as receiving, determining, rendering, displaying and the like, consistent with the manner employed by those skilled in the art. Quantities may take the form of electrical, magnetic, or optical signals capable of being stored, transferred, combined, and/or otherwise manipulated through mechanical, electrical and/or optical components of a processor based device.

Various operations may be described as multiple discrete steps in turn, in a manner that may be helpful in understanding embodiments of the present invention; however, the order of description should not be construed to imply that these operations are order dependent.

The description may use the phrases "in an embodiment," or "in embodiments," which may each refer to one or more of the same or different embodiments. Furthermore, the terms "comprising," "including," "having," and the like, as used with respect to embodiments of the present invention, are synonymous.

In an embodiment of the present invention, a storage server may be employed to facilitate users of client devices in sending partially or fully secure electronic messages to one or more recipients. Similarly, a user (i.e. "sender") of a messaging client (i.e. "sending client") incorporated with the teachings of the present invention may be able to compose an electronic message to be delivered to one or more recipients in either a fully secured or partially secured manner. Furthermore, the sender may employ one or more predefined or custom generated forms as a basis for the electronic message and/or a message delivery notification designed to alert the recipient(s) of the availability of the electronic message and any possible attachments. In an embodiment of the present invention, a sender may require certain inputs to be entered by an intended recipient of a secure message (whether fully or partially secure), such as passwords or answers to survey questions, before the recipient may be provided with the secure message. In an embodiment of the present invention, the sender may elect to have the content of the delivered message be dependent upon the inputs provided by the recipient prior to delivery of the message. In an embodiment of the present invention, a split encryption key methodology may be utilized in which secure messages or portions of messages may be stored in an encrypted form on the storage server in conjunction with only a portion of the access information necessary to access a given secure message. Other encryption methods may be employed in embodiments of the present invention depending on the desired application.

In the following description including the claims, unless further particularized or otherwise noted, the term "message" is intended to broadly refer to electronic messages, email messages, attachments and/or data files in whole or in part, whether or not they comprise a text, binary, or otherwise encoded form, and whether or not they are transmitted via the Simple Mail Transport Protocol (SMTP), HTTP, file transfer protocol (FTP), trivial file transfer protocol (TFTP), or otherwise.

FIG. 1 is a block diagram illustrating a messaging system in accordance with an embodiment of the present invention. In an embodiment of the present invention, messaging component 100 may be equipped to facilitate the composition, for example by a user, and transmission of messages and/or data to one or more recipients 130. In an embodiment of the present invention, messaging component 100 may be equipped with secure messaging services including message notification and form generation logic to facilitate the exchange of secure messages. Recipient(s) 130 may represent one or more computing devices equipped with a generic user agent to receive and transmit messages.

In an embodiment of the present invention, messaging component 100 may access a variety of heterogeneous documents for attachment in one or more messages directly from various data source(s) and/or data store(s) 120, and/or from a database 110. Database 110 may additionally contain data in any variety of suitable formats and/or structures. Database 110 may also point to and/or receive data from various data source(s) and/or data store(s) 120.

For the purposes of various embodiments of the present invention, the term "heterogeneous documents" refers to documents that differ, for example, in form, format, and/or data structure. For example, embodiments of the present invention enable the use of heterogeneous documents in messaging and thus do not force the use of a common data structure or format, such as using PDF documents, in a message.

In an exemplary embodiment of the present invention, a messaging component 100 may be clinical messaging software for use by health care providers, such as physicians, nurses, administration staff, etc. A recipient may be, for example, a patient or another provider. In an embodiment of the present invention, a suitable database may be a clinical database or an electronic heath records system that provides for integration with other data sources and/or data stores. Thus, according to an embodiment of the present invention, a clinical messaging component may be integrated with an electronic health records system and linked with associated sources and/or stores of data, documents, etc. such that the clinical messaging component may package the data in a message to be delivered to a recipient. According to embodiments of the present invention, the term "clinical" should be given broad interpretation as related to health or medical care.

Figure 2:
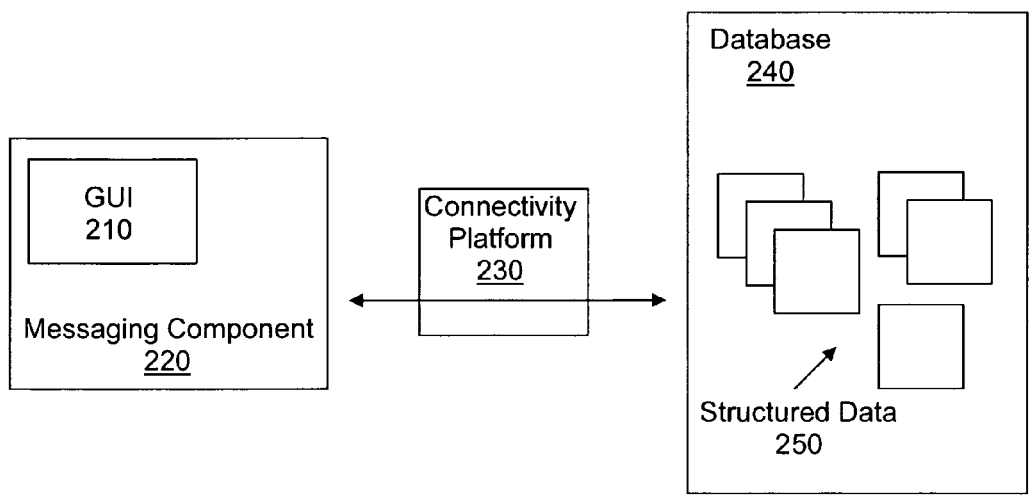
FIG. 2 illustrates an integrated messaging component for selection and attachment of various documents to an electronic message in accordance with an embodiment of the present invention.

FIG. 2 illustrates an integrated messaging component for selection and attachment of various documents to an electronic message in accordance with an embodiment of the present invention. In an embodiment of the present invention as shown in FIG. 2, a graphical user interface 210 may be provided to facilitate the selection and attachment of various documents to an electronic message. Graphical user interface 210 may run as part of messaging component 220. Message component 220 may be a standalone messaging component or integrated with an application or a suite of applications. Connectivity platform 230 provides a platform for integration of components, such as messaging component 220 and database 240 according to an embodiment of the present invention. In an embodiment of the present invention, messaging component 220 may be a clinical messaging component and/or database 240 may be a clinical database.

In an embodiment of the present invention, a user may access graphical user interface (GUI) 210 and, from GUI 210, may create an electronic message, and/or select documents for attachment to the electronic message. In order to send attachments with the electronic message, messaging component 220 interfaces via connectivity platform 230 with database 240 to return views and/or structured lists identifying documents available for attachment in the electronic message. According to an embodiment of the present invention, documents available for attachment may be represented in a variety of formats or views, including lists, icons, files, etc. In embodiments of the present invention, the formats and/or lists may provide views of multi-tiered data from database 240.

In an embodiment of the present invention, database 240 may store data in a structured format 250, such as structured patient data as in a patient's medical records. For example, a patient's medical records may include physician's notes, diagnostic test results, laboratory reports, etc. In such an embodiment, users may include physicians, administrators, nurses, medical office staff, etc.

In an embodiment of the present invention, documents identified in various lists and/or views may be stored in a variety of locations, and in a variety of different formats, and connectivity platform 230 may provide for extraction of those documents and return of those documents to messaging component 220 for attachment in an electronic message.

Whether operating in a messaging component, such as a clinical messaging component, or in a database or data store, an embodiment of the present invention provides a method to relate various stored documents and/or documents attached in an electronic message with each other. Documents may be related to each other in a variety of ways, including establishing a cross-related document nomenclature, storing related documents in files or in a structured hierarchy, etc. In an embodiment of the present invention, when a document is stored or attached in an electronic message, the document is examined to determine whether it has been associated with an entity (e.g. a patient). If the document has not been associated with an entity, an identifier identifying the entity may be injected into the document. Such an identifier provides for a mechanism to relate multiple heterogeneous documents to each other, as well as document search and discovery functions based on the identifier.

Figure 3:
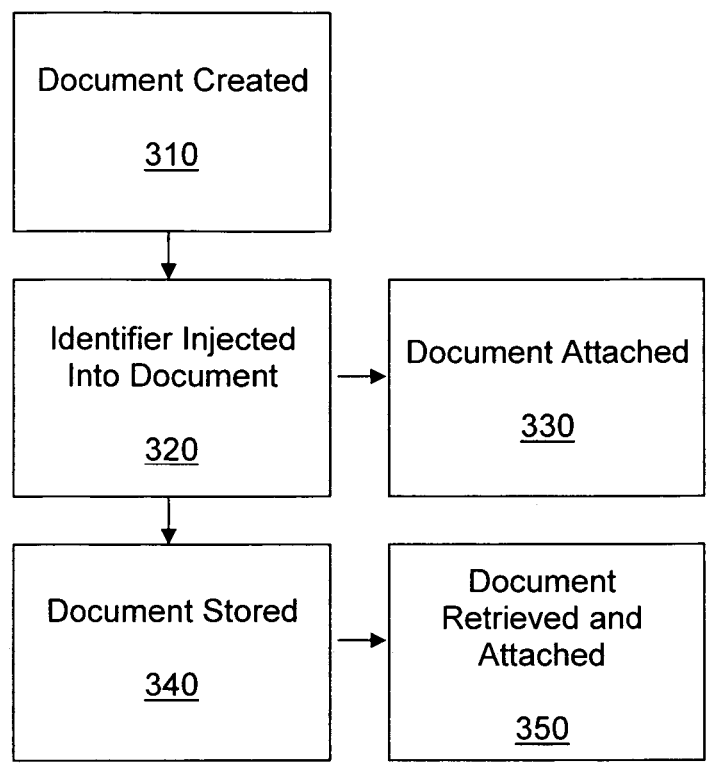
FIG. 3 illustrates a flowchart of an integrated document identification and attachment method in accordance with an embodiment of the present invention.

FIG. 3 illustrates a flowchart of a document identification and attachment method in accordance with an embodiment of the present invention. In block 310, a document may be created by any of a variety of systems. According to en embodiment of the present invention, a document may be any document, such as a word processing file, an image file, a text document, an RTF document, a spreadsheet, a database, etc. As described earlier, the document may be examined to determine whether it has been associated with an entity (e.g. a patient). If the document has not been associated with an entity, an identifier 320 may be embedded in the created document, for example, in the document header, in a package header, and/or as metadata or a metadata tag. The identifier may be unique to the document, or, in an embodiment of the present invention, may be an identifier that is unique to a set of documents to provide inter-relatability of those documents. For example, in an embodiment of the present invention, the documents may be individual components of a patient's medical chart and the identifier may be a patient identifier. In such embodiments, the documents may be searched and sorted based on the identifier, and thus may be stored in disparate locations while still maintaining the relational element. In embodiments of the present invention, one or more identifier(s) may be used in a document. In various embodiments, the identifier is derived from a current context of an application, e.g. an application having the messaging component integrated. More specifically, in embodiments in which the messaging component is integrated with a clinical application, the identifier may be the current patient identifier of the records and/or data being viewed and/or processed.

In various embodiments, to facilitate support of a variety of heterogeneous documents, the document may be further translated into a desired common attachment format. In various embodiments, the desired common attachment format may employ XML or XML-like tags designating various portions of a document, such as metadata and/or the document body.

Once a document has been embedded with an identifier and/or translated into a desired common attachment format, the document may be attached to an electronic message (block 330). In an embodiment of the present invention, the document may be stored (block 340) in a variety of data stores. The document may then be accessed from its storage location and attached to an electronic message (350). Since the identifier is contained in the document, the relatability of documents containing the identifier may be maintained through creation, transmission and receipt of the electronic message. As such, the recipient of the message may take advantage of the relational aspects of the identifiers provided in the documents.

Some documents, however, are dynamically generated. For example, some applications may provide viewable reports that may be printed in hard copy or paper form, and/or printed to a file. In an embodiment of the present invention, to further enhance the usability of embodiments of the present invention, a print driver is provided and/or enhanced for an application to allow dynamically generated documents to be automatically embedded with an identifier associating the document with an entity, and/or translated to a desired common attachment form, as earlier described.

Figure 4:
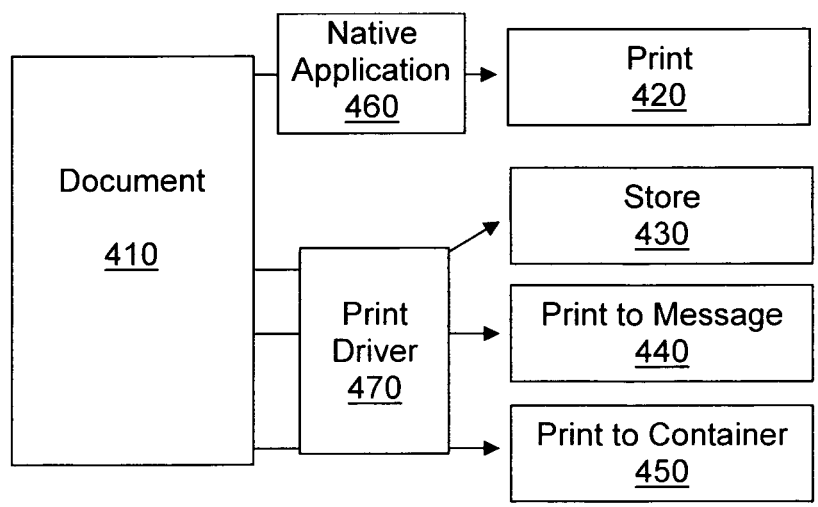
FIG. 4 illustrates various print and/or storage options using an integrated print driver in accordance with an embodiment of the present invention.

FIG. 4 illustrates various print and/or storage options using an integrated print driver in accordance with an embodiment of the present invention. FIG. 4 illustrates various print and/or storage options 420, 430, 440, and 450 for document 410. Document 410 may be directly printed via the native application 460 from which document 410 was generated. In an embodiment as shown in FIG. 4, the native application 460 does not provide for document 410 to be saved or attached in an electronic message. Thus, an integrated print driver 470 may be provided in accordance with an embodiment of the present invention to enable operations 430, 440, and 450. Print driver 470 embeds the proper identifiers, and/or translates the electronic substance of document 410 into a format that may be stored or attached to an electronic message. For example, document 410 may be "electronically printed" or translated into a PDF, or other suitable format, that may be stored in a variety of locations on a computer or portable storage device, such as a disk, diskette, CD-ROM, etc. According to an embodiment of the present invention, a stored document may then be retrieved and attached to an electronic message as desired.

In an embodiment of the present invention, document 410 may be electronically printed directly to an electronic message (440). In such an embodiment, a document that was previously unable to be stored or was unattachable may be rendered as an attachment via operation of print driver 470 and thus may be directly attached to an electronic message. Alternatively, according to an embodiment of the present invention, print driver 470 may allow document 410 to be printed to a container (450). A container allows multiple documents to be captured in an integrated data store from which one or more documents may be selected for attachment to an electronic message. In an embodiment of the present invention, a container may be referred to as a briefcase, and may be represented graphically with a briefcase graphic or icon.

In an embodiment of the present invention, a container may be associated with a particular document identifier. In a further embodiment of the present invention, a container may itself be provided with an identifier that is the same or different in substance and/or format from the document identifier(s). In an embodiment of the present invention, a container may be provided with the same identifier as the documents intended to be stored in the container. In a further embodiment of the present invention, a container may be provided with an identifier to match to a document(s) identifier and the container may be configured to only allow attachment or storage of those documents having the same identifier as the container. Such an embodiment increases security and reduces error by ensuring that all documents printed to, or attached to a container share the same identifier and match the container identifier. In still other embodiments, a container may be provided for a situation in which a user selects documents for attachment to electronic messages via a GUI, as earlier described referencing FIGS. 1 and 2.

Figure 5:
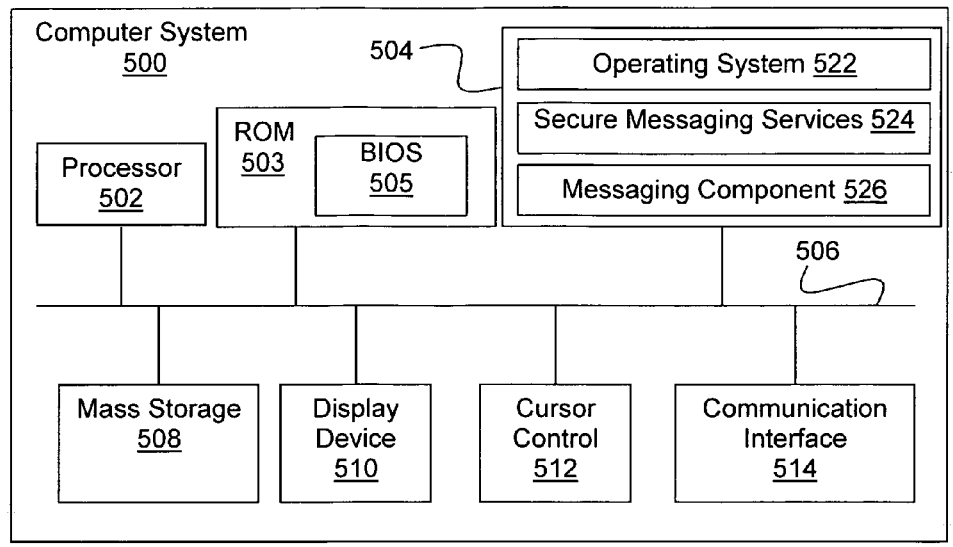
FIG. 5 illustrates an exemplary computer system suitable for use as a sending client or storage server in accordance with embodiments of the present invention.

FIG. 5 illustrates an exemplary computer system suitable for use as a sending or recipient client or server in accordance with embodiments of the present invention. As shown, example computer system 500 includes processor 502, ROM 503 including basic input/output system (BIOS) 505, and system memory 504 coupled to each other via "bus" 506. Also coupled to "bus" 506 are non-volatile mass storage 508, display device 510, cursor control device 512 and communication interface 514. During operation, memory 504 may also include working copies of operating system 522, messaging component 526, and (client side of) secure messaging services 524. In various embodiments, memory 504 may also include one or more applications (not shown), with which messaging component 526 is integrated or coupled. In the case of the sending client, secure messaging services 524 may include message notification and form generation logic in accordance with embodiments of the present invention to facilitate the exchange of secure messages between a sending client, storage server, and one or more recipients. In the case of a storage server, messaging services 524 facilitate storage and encryption of messages/data on behalf of a sending client, and the generation of one or more encryption keys to facilitate recipient access to the encrypted messages/data. In other embodiments, system 500 may also include an electronic health records system.

Figure 6:
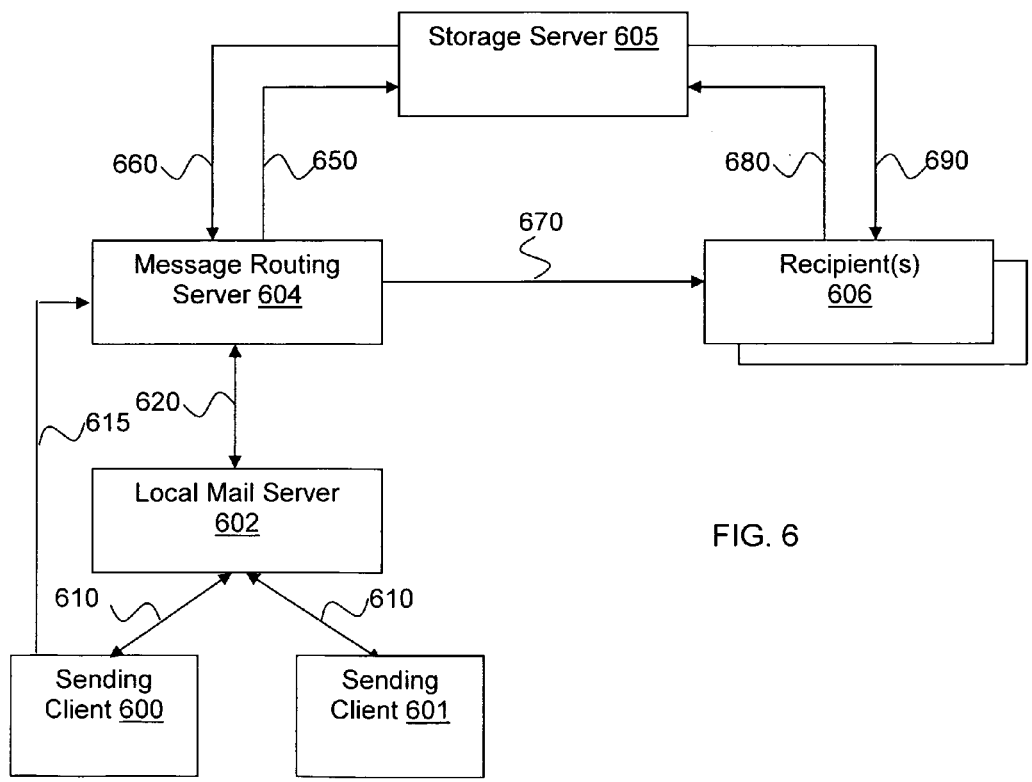
FIG. 6 illustrates an enterprise based secure messaging system including various logical device interactions in accordance with an embodiment of the present invention.

In accordance with an embodiment of the present invention, an enterprise based secure messaging system may be provided. The enterprise secure messaging system may be practiced in conjunction with the messaging systems and methods described herein. FIG. 6 illustrates an enterprise based secure messaging system including various logical device interactions, in accordance with an embodiment of the present invention. In accordance with an embodiment of the present invention, local mail server 602 represents a server equipped with electronic mail services, such as those provided by Exchange from Microsoft Corporation or Domino from IBM Corporation, to receive outgoing message transmission requests from clients 600 and 601, to receive incoming messages to be delivered to clients 600 and 601, and to temporarily store or queue both the outgoing and incoming messages until such time that the message destination domains/devices may be determined and contacted.

Message routing server 604 represents a server that may route mail traffic from local mail server 602 (and sending clients 600 and 601) to storage server 605 and recipients 606, much like a mail gateway. In an embodiment of the present invention, outgoing messages from local mail server 602 are first directed to message routing server 604 before they are delivered to storage server 605 and/or recipients 606.

In an embodiment of the present invention, a sender corresponding to either sending client 600 or 601 may compose an electronic message addressed to one or more recipients 606, that may first be delivered to local mail server 602 (610). In an embodiment of the present invention, local mail server 602 may unconditionally transmit (e.g. via redirection or forwarding) messages it receives to message routing server 604, whereas in another embodiment of the present invention, mail server 602 may transmit messages to message routing server 604 based upon whether or not the message is to be stored and/or delivered in a secure manner by storage server 605. In an embodiment of the present invention, sending client 600/601 may transmit an HTTP-based request directly (e.g. via a browser application) to message routing server 604 identifying the message to be securely stored and delivered, effectively bypassing local mail server 602 (615).

In an embodiment of the present invention, message routing server 604 may determine (based, for example, upon a variety of criteria such as source or destination address, content of the message, size of the message, etc.) whether a particular message is to be stored and delivered by storage server 605 in a secure manner. In an embodiment of the present invention, an SMTP or HTTP-based message may include an identifier (e.g. in an associated header field) that indicates to message routing server 604 whether the message is to be securely stored and delivered in accordance with the teachings of embodiments of the present invention.

If it is determined that an identified message is to be securely stored and/or delivered, message routing server 604 may transmit a request to storage server 605 to store the identified message (or portion of a message) securely (650). In an embodiment of the present invention, in response to the request of message routing server 604, storage server 605 may securely store the identified message and generate access data associated with the securely stored message. In an embodiment of the present invention, the access data may be represented by an access token that may include just the access data or supplemental information in addition to the access data. In an embodiment of the present invention, storage server 605 may encrypt the message, for example, using a split encryption key having two or more key portions, with storage server 605 retaining a first key portion and transmitting a second key portion to the sending client. In other embodiments of the present invention, however, storage server 605 may employ other encryption methods or other means of securely storing the message besides encryption.

Once generated, the access token may be returned to message routing server 604 by storage server 605 (660). In an embodiment of the present invention, storage server 605 may combine/integrate the access token with a message notification and transmit the integrated message notification to message routing server 604. In another embodiment of the present invention, storage server 605 may transmit the access token to message routing server 604 where message routing server 604 integrates the access token with a message notification. In various embodiments of the present invention, the message notification may be selected from one or more predefined notifications or it may be dynamically or manually generated by storage server 605 and/or message routing server 604. In an embodiment of the present invention, where multiple such message routing servers are utilized by various subsidiaries of a parent company for example, each message routing server may be configured to generate subsidiary-specific notifications notwithstanding that the message routing servers are each associated with the same storage server.

Once the access token is returned to message routing server 604, message routing server 604 may transmit the integrated notification to one or more of recipients 606 to facilitate recipient access to the message (670). In an embodiment of the present invention, message notifications may be delivered from message routing server 604 to one or more recipients 606 in the form of electronic mail messages using, for example, an email based communications protocol such as SMTP or X.400. Once a recipient has received a message notification in, for example, their email inbox, the recipient may open and view the message notification as they would with any other email message. In an embodiment of the present invention, the recipient may utilize a user input device such as a mouse to select a hyperlink or one or more controls incorporated within the notification to initiate retrieval of one or more corresponding secure messages stored by storage server 605. In an embodiment of the present invention, the token may be submitted to storage server 605 by one or more of recipients 606 in response to recipient input (680).

In response to receiving the access token from the one or more recipients 606, storage server 605 may then transmit the corresponding secure message (or a portion thereof) to one or more indicated recipients 606 (690). In an embodiment of the present invention, communications between message routing server 604 and storage server 605, as well as communications between recipients 606 and storage server 605, may occur in accordance with a first communication protocol such as HTTP, whereas communications between message routing server 604 and recipients 606 may occur in accordance with a second communication protocol such as SMTP.

In an embodiment of the present invention, in addition to storage server 605 returning the access token to message routing server 604 (660), storage server 605 may further return one or more control parameters or instructions to message routing server 604 to indicate whether any post-processing in association with the message may be performed. In an embodiment of the present invention, storage server 605 may return one or more control parameters or instructions to message routing server 604 to cause message routing server (e.g. via local mail server 602 or directly) to return a message to sending client 600/601 that may include an access token to facilitate client 600/601 in accessing information as to the status of the corresponding message. In an embodiment of the present invention, message routing server 604 may return a message identifier and the first encryption key portion to the sending client 600/601 for use, for example, by the sender in obtaining log information about the associated message, such as whether a recipient has read the message or forwarded the message to another recipient.

In various embodiments, various aspects of the present invention may be implemented in discrete hardware or firmware. For example, one or more application specific integrated circuits (ASICs) may be programmed with one or more of the above-described functions of the embodiments of the present invention. In another example, one or more functions of the embodiments of the present invention may be implemented in one or more ASICs on additional circuit boards and the circuit boards may be inserted into the computer(s) described above. In another embodiment of the present invention, programmable gate arrays may be used to implement one or more functions of embodiments of the present invention. In another embodiment of the present invention, a combination of hardware and software may be used to implement one or more functions of embodiments of the present invention.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the present invention. Those with skill in the art will readily appreciate that embodiments in accordance with the present invention may be implemented in a very wide variety of ways. This application is intended to cover any adaptations or variations of the embodiments discussed herein. Therefore, it is manifestly intended that embodiments in accordance with the present invention be limited only by the claims and the equivalents thereof.

What is claimed is:

1. A system, comprising:
one or more storage devices having one or more clinical databases adapted to store a plurality of heterogeneous clinical documents for a plurality of patients, with at least one patient having multiple heterogeneous clinical documents; and
a clinical client device coupled to the one or more storage devices, including a client side of a secure messaging service and a clinical document attachment service, wherein the client side of the secure messaging service is adapted to facilitate a clinical service provider in creatin and secure providing one or more electronic clinical messages to one or more recipients via a server side of the secure messaging service, and the clinical document attachment service is adapted to enable and facilitate selective attachment of heterogeneous clinical documents to the one or more electronic clinical messages,
wherein the clinical document attachment service includes an identifier generation service for embedding an identifier of a patient in each of the plurality of heterogeneous clinical documents, and wherein the clinical document attachment service is adapted to determine whether a clinical document has an embedded patient identifier, and invoke the identifier generation service to embed a patient identifier when determining a clinical document does not have an embedded patient identifier, the same identifier embedded in each of a plurality of documents associated with an individual patient; and
wherein the server side of the secure messaging service is adapted to secure an electronic clinical message with a split key having a first and a second key portion, and provide a notification to the recipient with one of the key portions for use to retrieve the electronic clinical message.

2. The system of claim 1, wherein said clinical databases are part of an electronic health records system.

3. The system of claim 1, wherein said clinical client device further comprises a graphical user interface for selectively accessing said clinical documents for attachment to one or more electronic clinical messages.

4. The system of claim 1, wherein the clinical document attachment service includes a document attachment generation service adapted to translate a clinical document into an attachable form for attachment to an electronic clinical message.

5. The system of claim 4, wherein the document attachment generation service comprises a print driver invocable from a clinical application.

6. The system of claim 1, wherein the server side of the secure messaging service determines whether the electronic clinical message is to be secured based on context.

7. The system of claim 1, wherein the server side of the secure messaging service determines whether the electronic clinical message is to be secured based on an identifier in the electronic clinical message.

8. The system of claim 1, wherein the server side of the secure messaging service returns one of the key portions of the split key to the clinical service provider to facilitate access to information regarding the status of the electronic clinical message.

9. A computer implemented method, comprising:
facilitating, by a client side of a secure messaging service operating on a client device, a sender in creating a clinical message;
examining, by a document examination service operating on the client device, an electronic version of a first document to determine whether the electronic version has an embedded identifier associating the first document with an entity, wherein the electronic version of the first document is to be attached to the electronic clinical message;
conditionally embedding, by an identifier generation service operating on the client device, an identifier identifying the entity in the electronic version of the first document to associate said first document with the entity;
examining, by the document examination service, an electronic version of a second document to determine whether the electronic version has the embedded identifier associating the second document with the entity, wherein the electronic version of the second document is to be attached to the electronic clinical message;
conditionally embedding, by the identifier generation service, the identifier identifying the entity in the electronic version of the second document to associate said second document with the entity;
attaching, by a clinical document attachment service operating on the client device, the electronic versions of the first and second documents to said electronic clinical message; and
securely transmitting the electronic clinical message, by the client side of the secure messaging service, to a recipient, wherein the secure transmission is in cooperation of with a server side of the secure messaging service which employs a split key having a first and a second key portion to secure the clinical electronic message.

10. The method of claim 9, further comprising extracting, by the identifier generation service, the identifier from a current application context of the first document and/or second document.

11. The method of claim 9, wherein said embedding comprises embedding the identifier as metadata of the electronic versions of the first and second documents.

12. The method of claim 9, wherein said first and second documents comprise heterogeneous documents associated with a particular medical patient.

13. The method of claim 9, further comprising storing, by the clinical document attachment service, the first document and the second document in an electronic container.

14. The method of claim 13, wherein the electronic container also includes the identifier identifying the entity.

15. The method of claim 14, wherein the electronic container only permits storage of documents embedded with the identifier identifying the entity.

16. The method of claim 9, wherein the secure transmission of the electronic clinical message comprises the server side of the secure messaging service retaining the first key portion and transmitting the second key portion.

17. The method of claim 16, further comprises the server side of the secure messaging service returning one or more control parameters or instructions to the sender to facilitate accessing information regarding the status of the electronic message.

* * * * *

UNITED STATES PATENT AND TRADEMARK OFFICE
CERTIFICATE OF CORRECTION

PATENT NO. : 8,510,387 B2  
APPLICATION NO. : 11/194117  
DATED : August 13, 2013  
INVENTOR(S) : Murali M. Karamchedu et al.

Page 1 of 1

It is certified that error appears in the above-identified patent and that said Letters Patent is hereby corrected as shown below:

In the claims

In column 10, line 37, in claim 9, before "with" delete "of".

Signed and Sealed this
Twenty-ninth Day of December, 2015

Michelle K. Lee
*Director of the United States Patent and Trademark Office*